United States Patent [19]

Lopez

[11] Patent Number: 5,211,739
[45] Date of Patent: May 18, 1993

[54] HERBICIDAL-1-(DISUBSTITUTED CARBAMOYL OR THIOCARBAMOYL)-1,2,4-TRIAZOL-3-YL SULFONATES AND THISULFONATES

[75] Inventor: Raul C. G. Lopez, Doylestown, Pa.

[73] Assignee: Rohm and Haas Company, Philadelphia, Pa.

[21] Appl. No.: 766,948

[22] Filed: Sep. 27, 1991

[51] Int. Cl.$^5$ ............... C07D 249/12; C07D 401/02; C07D 403/02; A01N 43/653

[52] U.S. Cl. .................... 504/273; 546/210; 548/263.2; 504/249; 504/191

[58] Field of Search ............ 548/263.2; 71/92; 546/210

[56] References Cited

U.S. PATENT DOCUMENTS

| | | | |
|---|---|---|---|
| 3,308,131 | 3/1967 | McKusick | 546/210 |
| 3,952,001 | 4/1976 | Brookes et al. | 71/92 |
| 4,280,831 | 7/1981 | Patel | 71/92 |
| 4,810,271 | 3/1989 | Nakayama et al. | 71/92 |

OTHER PUBLICATIONS

Derwent Alerting Abstracts Bulletin, Chemical Patents Index, No. 84-092381/15 of Japanese Patent 59-39880, dated Mar., 1984.
Derwent Alerting Abstracts Bulletin, Chemical Patents Index, No. 86-249722/38 of Japanese Patent 61-178980, dated Aug., 1986.

Primary Examiner—Mary C. Lee
Assistant Examiner—Lenora Ava Miltenberger
Attorney, Agent, or Firm—Clark R. Carpenter; Terence P. Strobaugh; Polly E. Ramstad

[57] ABSTRACT

This invention relates to 1-(disubstituted carbamoyl or thiocarbamoyl)-1,2,4-triazol-3-yl sulfonates and thiosulfonates of the formula

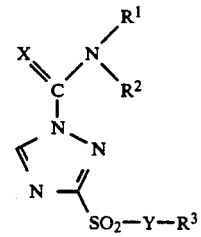

wherein $R^1$ and $R^2$ are each independently selected from the group consisting of optionally substituted alkyl, alkenyl, alkynyl, cycloalkyl, cycloalkenyl and cycloalkynyl, or they may together with the nitrogen to which they are attached form an optionally substituted heterocyclic ring, $R^3$ is an optionally substituted alkyl, cycloalkyl, alkenyl, cycloalkenyl, aryl, aralkyl or aromatic heterocyclic group, X and Y are each independently oxygen or sulfur, and the agronomically acceptable acid addition salts and metal complexes thereof, compositions containing these compounds and their uses as herbicides.

15 Claims, No Drawings

HERBICIDAL-1-(DISUBSTITUTED CARBAMOYL OR THIOCARBAMOYL)-1,2,4-TRIAZOL-3-YL SULFONATES AND THISULFONATES

FIELD OF THE INVENTION

This invention relates to 1-(disubstituted carbamoyl or thiocarbamoyl)-1,2,4-triazol-3-yl sulfonates and thiosulfonates, their acid addition salts and metal complexes, compositions containing these compounds, and the use of these compounds as herbicides.

BACKGROUND OF THE INVENTION

Chemical weed control agents enable more efficient crop production by elimination of competing plant growth. During the past years, there has been an intensified search for herbicides to control unwanted plants.

A number of carbamoyl substituted triazoles are known to be useful as herbicides. For example, Nakayama et al., U.S. Pat. No. 4,810,271, disclose as herbicides dialkylcarbamoyl triazoles substituted by alkylsulfonyl, -sulfinyl and -thio groups. Brookes et al., U.S. Pat. No. 3,952,001, disclose as herbicides a broad group of 1-disubstitutedcarbamoyl-3-substituted triazoles including 3-alkylthio, alkylsulphinyl, alkylsulphonyl, alkenylthio and disubstituted 3-sulfonamides. Patel, U.S. Pat. No. 4,280,831, discloses as a herbicide the single compound 3-benzylsulfonyl-1-diethylcarbamoyl-1,2,4-triazole. McKusick, U.S. Pat. No. 3,308,131, discloses as insecticides a broad group of 1-carbamoyl-3-substituted-1,2,4-triazoles. Derwent Alerting Abstracts Bulletin, Chemical Patents Index, Number 84-092381/15 of Japanese Patent 59-39880 discloses as herbicides a broad group of 1-carbamoyl-3-(substituted benzylsulfonyl, -sulfinyl and -thio)-1,2,4-triazoles. Derwent Alerting Abstracts Bulletin, Chemical Patents Index, Number 86-249722/38 of Japanese Patent 61-178980 discloses as herbicides a broad group of 1-carbamoyl-3-(substituted heterocyclylalkylsulfonyl, -sulfinyl and -thio)-1,2,4-triazoles. None of this art suggest the specific class of substituted triazole sulfonates and thiosulfonates of the present invention.

SUMMARY OF THE INVENTION

This invention relates to 1-(disubstituted carbamoyl or thiocarbamoyl)-1,2,4-triazol-3-yl sulfonates and thiosulfonates of the formula

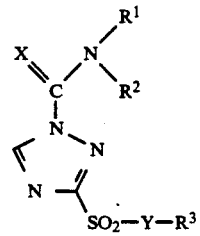

(I)

wherein $R^1$ and $R^2$ are each independently selected from the group consisting of alkyl, alkenyl, alkynyl, cycloalkyl, cycloalkenyl, alkylcycloalkyl, alkenylcycloalkyl, alkynylcycloalkyl, haloalkyl, haloalkenyl, haloalkynyl, halocycloalkyl, alkoxyalkyl, alkoxyalkenyl, alkoxyalkynyl, alkoxycycloalkyl, haloalkoxyalkyl, haloalkoxyalkenyl, haloalkoxyalkynyl, haloalkoxycycloalkyl, cycloalkylalkyl, cycloalkenylalkyl, alkycycloalkylalkyl, alkenylcycloalkylalkyl, alkynylcycloalkylalkyl, halocycloalkylalkyl and alkoxycycloalkylalkyl, or a $(C_4-C_5)$alkylene group or a $(C_4-C_5)$alkylene group substituted with one or two substituents each independently selected from the group consisting of alkyl, alkenyl, alkynyl, cycloalkyl, alkoxy, halo and haloalkoxy, so as to form a nitrogen-containing five or six membered cyclic ring with the nitrogen to which they attach, $R^3$ is alkyl, haloalkyl, cycloalkyl, halocycloalkyl, alkenyl, cycloalkylalkenyl, alkoxyalkenyl, haloalkenyl, cycloalkenyl, halocycloalkenyl, aryl, aralkyl, or aryl or aralkyl both substituted on the aryl ring with one to three substituents each independently selected from the group consisting of alkyl, alkenyl, alkynyl, cycloalkyl, halo, haloalkyl, alkoxy, haloalkoxy, cyano, nitro, alkoxycarbonyl, alkylthio and haloalkylthio, X and Y are each independently oxygen (O) or sulfur (S), and the agronomically acceptable acid addition salts and metal complexes thereof, compositions containing these compounds and their uses as herbicides.

DETAILED DESCRIPTION OF THE INVENTION

This invention relates to compounds of the general formula (I) wherein $R^1$ and $R^2$ are each independently selected from the group consisting of $(C_1-C_6)$alkyl, $(C_2-C_4)$alkenyl, $(C_2-C_4)$alkynyl, $(C_3-C_6)$cycloalkyl, $(C_5-C_6)$cycloalkenyl, $(C_1-C_3)$alkyl$(C_3-C_6)$cycloalkyl, $(C_2-C_3)$alkenyl$(C_3-C_6)$cycloalkyl, $(C_2-C_3)$alkynyl$(C_3-C_6)$cycloalkyl, halo$(C_1-C_4)$alkyl, halo$(C_2-C_4)$alkenyl, halo$(C_2-C_4)$alkynyl, halo$(C_3-C_6)$cycloalkyl, $(C_1-C_4)$alkoxy$(C_1-C_6)$alkyl, $(C_1-C_4)$alkoxy$(C_2-C_4)$alkenyl, $(C_1-C_4)$alkoxy$(C_2-C_4)$alkynyl, $(C_1-C_4)$alkoxy$(C_3-C_6)$cycloalkyl, halo$(C_1-C_4)$alkoxy$(C_1-C_6)$alkyl, halo$(C_1-C_4)$alkoxy$(C_2-C_4)$alkenyl, halo$(C_1-C_4)$alkoxy$(C_2-C_4)$alkynyl, halo$(C_1-C_4)$alkoxy$(C_3-C_6)$cycloalkyl, $(C_3-C_6)$cycloalkyl$(C_1-C_4)$alkyl, $(C_5-C_6)$cycloalkenyl$(C_1-C_4)$alkyl, $(C_1-C_4)$alkyl$(C_3-C_6)$cycloalkyl$(C_1-C_4)$alkyl, $(C_2-C_4)$alkenyl$(C_3-C_6)$cycloalkyl$(C_1-C_4)$alkyl, $(C_2-C_4)$alkynyl$(C_3-C_6)$cycloalkyl$(C_1-C_4)$alkyl, halo$(C_3-C_6)$cycloalkyl$(C_1-C_4)$alkyl and $(C_1-C_4)$alkoxy$(C_3-C_6)$cycloalkyl$(C_1-C_4)$alkyl, or $R^1$ and $R^2$ may together represent a $(C_4-C_5)$alkylene group or a $(C_4-C_5)$alkylene group substituted with one or two substituents each independently selected from the group consisting of $(C_1-C_4)$alkyl, $(C_2-C_4)$alkenyl, $(C_2-C_4)$alkynyl, $(C_3-C_6)$cycloalkyl, $(C_1-C_4)$alkoxy, halo and halo$(C_1-C_4)$alkoxy, so as to form a nitrogen-containing five or six membered cyclic ring with the nitrogen to which they attach, $R^3$ is $(C_1-C_8)$alkyl, halo$(C_1-C_4)$alkyl, $(C_3-C_6)$cycloalkyl, halo$(C_3-C_6)$cycloalkyl, $(C_2-C_4)$alkenyl, $(C_3-C_6)$cycloalkyl$(C_2-C_4)$alkenyl, $(C_1-C_4)$alkoxy$(C_2-C_4)$alkenyl, halo$(C_2-C_4)$alkenyl, $(C_3-C_6)$cycloalkenyl, halo$(C_3-C_6)$cycloalkenyl, $(C_6-C_{10})$aryl, $(C_6-C_{10})$ar$(C_1-C_6)$alkyl, or $(C_6-C_{10})$aryl or $(C_6-C_{10})$ar$(C_1-C_6)$alkyl both substituted on the aryl ring with one to three substituents each independently selected from the group consisting of $(C_1-C_6)$alkyl, $(C_2-C_4)$alkenyl, $(C_2-C_4)$alkynyl, $(C_3-C_6)$cycloalkyl, halo, halo$(C_1-C_4)$alkyl, $(C_1-C_4)$alkoxy, halo$(C_1-C_4)$alkoxy, cyano, nitro, $(C_1-C_6)$alkoxycarbonyl, $(C_1-C_4)$alkylthio and halo$(C_1-C_4)$alkylthio, X and Y are each independently oxygen (O) or sulfur (S), and the agronomically acceptable acid addition salts and metal complexes thereof.

A preferred embodiment of this invention is the compounds, salts and complexes of Formula (I) wherein $R^1$ and $R^2$ are each independently selected from the group consisting of $(C_1-C_4)$alkyl, $(C_2-C_4)$alkenyl, $(C_2-C_4)$alkynyl, $(C_5-C_6)$cycloalkyl, halo$(C_1-C_4)$alkyl, halo$(C_2-C_4)$alkenyl, halo$(C_2-C_4)$alkynyl, halo$(C_5-C_6)$cycloalkyl, $(C_1-C_2)$alkoxy$(C_1-C_4)$alkyl, $(C_1-C_2)$alkoxy$(C_2-C_4)$alkenyl, $(C_1-C_2)$alkoxy$(C_2-C_4)$alkynyl, $(C_1-C_2)$alkoxy$(C_5-C_6)$cycloalkyl, halo$(C_1-C_2)$alkoxy$(C_1-C_4)$alkyl, halo$(C_1-C_2)$alkoxy$(C_2-C_4)$alkenyl, halo$(C_1-C_2)$alkoxy$(C_2-C_4)$alkynyl, and halo$(C_1-C_2)$alkoxy$(C_5-C_6)$cycloalkyl, or $R^1$ and $R^2$ may together represent a $(C_4-C_5)$alkylene group or a $(C_4-C_5)$alkylene group substituted with one or two substituents each independently selected from the group consisting of $(C_1-C_2)$alkyl, $(C_1-C_2)$alkoxy, halo and halo$(C_1-C_2)$alkoxy, so as to form a nitrogen-containing five or six membered cyclic ring with the nitrogen to which they attach, $R^3$ is $(C_1-C_8)$alkyl, halo$(C_1-C_4)$alkyl or $(C_5-C_6)$cycloalkyl, phenyl, phenyl$(C_1-C_6)$alkyl, or phenyl or phenyl$(C_1-C_6)$alkyl both substituted on the phenyl ring with one to two substituents each independently selected from the group consisting of $(C_1-C_4)$alkyl, $(C_2-C_4)$alkenyl, $(C_2-C_4)$alkynyl, halo, halo$(C_1-C_2)$alkyl, $(C_1-C_4)$alkoxy, halo$(C_1-C_2)$alkoxy, cyano, nitro, $(C_1-C_4)$alkoxycarbonyl, $(C_1-C_2)$alkylthio and halo$(C_1-C_2)$alkylthio, X is O or S and Y is O.

A more preferred embodiment of this invention is the compounds, salts and complexes of Formula (I) wherein $R^1$ and $R^2$ are each independently selected from the group consisting of $(C_1-C_3)$alkyl, $(C_2-C_4)$alkenyl and $(C_2-C_4)$alkynyl, or $R^1$ and $R^2$ may together represent a $(C_4-C_5)$alkylene group or a $(C_4-C_5)$alkylene group substituted with one or two substituents independently selected from methyl and ethyl, so as to form a nitrogen-containing five or six membered cyclic ring with the nitrogen to which they attach, and $R^3$ is $(C_1-C_8)$alkyl, halo$(C_1-C_4)$alkyl, phenyl or phenyl substituted with one to two substituents each independently selected from the group consisting of $(C_1-C_3)$alkyl, halo, halo$(C_1-C_2)$alkyl, $(C_1-C_2)$alkoxy, halo$(C_1-C_2)$alkoxy, cyano, nitro, $(C_1-C_2)$alkoxycarbonyl, $(C_1-C_2)$alkylthio and halo$(C_1-C_2)$alkylthio.

An even more preferred embodiment of this invention is the compounds, salts and complexes of Formula (I) wherein $R^1$ and $R^2$ are each independently selected from the group consisting of methyl, ethyl, n-propyl, isopropyl, allyl and methallyl, or $R^1$ and $R^2$ may together with the nitrogen to which they attach represent a piperidyl group or a piperidyl group substituted with one or two methyl groups, and $R^3$ is ethyl, neopentyl, 2,2-dichloroethyl, 2,2,2-trichloroethyl, 2,2,3,3,3-pentafluoropropyl, 2,2,2-trifluoroethyl, 1,3-difluoro-2-propyl, phenyl or phenyl substituted with one to two substituents each independently selected from the group consisting of chloro, fluoro, bromo, methyl, isopropyl, trifluoromethyl, methoxy, methylthio, nitro, cyano and methoxycarbonyl.

A most preferred embodiment of this invention is the compounds, salts and complexes of Formula (I) wherein $R^1$ and $R^2$ are both ethyl, $R^3$ is phenyl, 3-methylphenyl, 4-methylphenyl, 4-(trifluoromethyl)phenyl, 4-fluorophenyl, 4-chlorophenyl, 3-methoxyphenyl, 4-methoxyphenyl, 4-(methylthio)phenyl, 2,2,2-trifluoroethyl or 1,3-difluoro-2-propyl, and X is O.

The term aryl as used in the present specification means an aromatic ring structure of six to ten carbon atoms, preferably a phenyl or naphthyl group. Typical aryl groups encompassed by this invention are phenyl, naphthyl, 2-chlorophenyl, 3-chlorophenyl, 4-chlorophenyl, 4-bromophenyl, 4-fluorophenyl, 2,3-dichlorophenyl, 2,3-difluorophenyl, 2,4-dichlorophenyl, 3,5-dichlorophenyl, 2,5-dichlorophenyl, 2,6-dichlorophenyl, 2,6-difluorophenyl, 3,4-dichlorophenyl, 2-methylphenyl, 3-methylphenyl, 4-methylphenyl, 2,4-dimethylphenyl, 2-chloro-6-methylphenyl, 2-methoxy-3-methylphenyl, 3-methoxy-2-methylphenyl, 3-(trifluoromethyl)phenyl, 4-(trifluoromethyl)phenyl, 2-(difluoromethoxy)phenyl, 4-cyanophenyl, 4-nitrophenyl, 4-methoxyphenyl, 4-(methylthio)phenyl, 4-isopropylphenyl, 2,4,6-trichlorophenyl, 4-iodophenyl, 4-fluoro-2-methylphenyl, 2-chloro-4-methylphenyl, 2-(fluoromethyl)phenyl, 4-(2-chloroethyl)phenyl, 4-t-butylphenyl, 4-t-butoxyphenyl, 2,4-dicyanophenyl, 4-allylphenyl, 4-propargylphenyl, 4-cyclopropylphenyl, 4-cyclohexylphenyl, 4-(chloromethylthio)phenyl, 2-(chloromethoxy)phenyl, 4-(methoxycarbonyl)phenyl and 3-isobutylphenyl.

The term aralkyl as used in the present specification means an alkyl group substituted with an aryl group, for example, $(C_6-C_{10})$ or $(C_1-C_6)$ alkyl such as 1-naphthylmethyl, 2-(4-chlorophenyl)ethyl and 6-(2,4-difluorophenyl)hexyl.

Alkyl includes straight and branched alkyl groups, for example $(C_1-C_8)$alkyl such as methyl, ethyl, n-propyl, isopropyl, n-butyl, isobutyl, sec-butyl, t-butyl, n-pentyl, isopentyl, neopentyl, n-hexyl, isohexyl, n-octyl and iso-octyl.

Halo means fluoro, chloro, bromo and iodo.

Alkenyl is, for example, $(C_2-C_4)$alkenyl such as vinyl, allyl, methallyl and 2-buten-1-yl.

Cycloalkylalkenyl is, for example, $(C_3-C_6)$cycloalkyl$(C_2-C_4)$alkenyl such as 1-cyclohexyl-1-propen-3-yl.

Alkoxyalkenyl is, for example, $(C_1-C_4)$alkoxy$(C_2-C_4)$alkenyl such as 4-ethoxy-2-buten-1-yl.

Alkynyl is, for example, $(C_2-C_4)$alkynyl such as propargyl.

Cycloalkyl is, for example, $(C_3-C_6)$cycloalkyl such as cyclopropyl, cyclopentyl and cyclohexyl.

Cycloalkenyl is, for example, $(C_5-C_6)$cycloalkenyl such as cyclopenten-3-yl and cyclohexen-3-yl.

Alkylcycloalkyl is, for example, $(C_1-C_3)$alkyl$(C_3-C_6)$cycloalkyl such as methylcyclopropyl, methylcyclopentyl and isopropylcyclohexyl.

Alkenylcycloalkyl is, for example, $(C_2-C_3)$alkenyl$(C_3-C_6)$cycloalkyl such as allylcyclopentyl and vinylcyclohexyl.

Alkynylcycloalkyl is, for example, $(C_2-C_3)$alkynyl$(C_3-C_6)$cycloalkyl such as propargylcyclohexyl.

Haloalkyl is, for example, halo($C_1$–$C_4$)alkyl such as trifluoromethyl, 2,2-dichloroethyl, 2,2,2-trichloroethyl, 2,2,3,3,3-pentafluoroethyl, 2,2,2-trifluoroethyl, 1,3-difluoro-2-propyl, chloromethyl, fluoromethyl, difluoromethyl, 1-chloroethyl, 1,1-difluoroethyl, 3-chloropropyl, 1-bromo-2-methylpropyl and 2,3-dichloropropyl.

Haloalkenyl is, for example, halo($C_2$–$C_4$)alkenyl such as 4-chloro-2-butenyl.

Haloalkynyl is, for example, halo($C_2$–$C_4$)alkynyl such as 4-bromo-2-butynyl.

Halocycloalkyl is, for example, halo($C_3$–$C_6$)cycloalkyl such as 2-chlorocyclopentyl.

Halocycloalkenyl is, for example, halo($C_3$–$C_6$)cycloalkenyl such as 1-chlorocyclopenten-3-yl.

Alkoxy is, for example, ($C_1$–$C_4$)alkoxy such as methoxy, ethoxy, n-propoxy, isopropoxy, n-butoxy, isobutoxy, sec-butoxy and t-butoxy.

Alkoxyalkyl is, for example, ($C_1$–$C_4$)alkoxy($C_1$–$C_6$)alkyl such as methoxymethyl and 4-isopropoxybutyl.

Alkoxyalkenyl is, for example, ($C_1$–$C_4$)alkoxy($C_2$–$C_4$)alkenyl such as 3-ethoxy-1-propen-1-yl.

Alkoxyalkynyl is, for example, ($C_1$–$C_4$)alkoxy($C_2$–$C_4$)alkynyl such as 4-n-propoxy-2-butyn-1-yl.

Alkoxycycloalkyl is, for example, ($C_1$–$C_4$)alkoxy($C_3$–$C_6$)cycloalkyl such as 4-ethoxycyclohexyl.

Haloalkoxy is, for example, halo($C_1$–$C_4$)alkoxy such as chloromethoxy, difluoromethoxy, 1,1-difluoroethoxy, trifluoromethoxy, 3-bromopropoxy, 1,3-dichloro-2-propoxy and 2,3-dichlorobutoxy.

Haloalkoxyalkyl is, for example, halo($C_1$–$C_4$)alkoxy($C_1$–$C_6$)alkyl such as fluoromethoxymethyl and 4-(2-chloroethoxy)butyl.

Haloalkoxyalkenyl is, for example, halo($C_1$–$C_4$)alkoxy($C_2$–$C_4$)alkenyl such as 4-methoxy-2-buten-1-yl.

Haloalkoxyalkynyl is, for example, halo($C_1$–$C_4$)alkoxy($C_2$–$C_4$)alkynyl such as 4-ethoxy-2-butyn-1-yl.

Haloalkoxycycloalkyl is, for example, halo($C_1$–$C_4$)alkoxy($C_3$–$C_6$)cycloalkyl such as 4-(difluoromethoxy)cyclopentyl.

Cycloalkylalkyl is, for example, ($C_3$–$C_6$)cycloalkyl($C_1$–$C_4$)alkyl such as cyclopropylmethyl and 2-(cyclohexyl)ethyl.

Cycloalkenylalkyl is, for example, ($C_5$–$C_6$)cycloalkenyl($C_1$–$C_4$)alkyl such as 2-cyclohexen-1-ylmethyl.

Alkylcycloalkylalkyl is, for example, ($C_1$–$C_4$)alkyl($C_3$–$C_6$)cycloalkyl($C_1$–$C_4$)alkyl such as 2-(4-isopropylcyclohexyl)ethyl.

Alkenylcycloalkylalkyl is, for example, ($C_2$–$C_4$)alkenyl($C_3$–$C_6$)cycloalkyl($C_1$–$C_4$)alkyl such as 2-allylcyclohexylmethyl.

Alkynylcycloalkylalkyl is, for example, ($C_2$–$C_4$)alkynyl($C_3$–$C_6$)cycloalkyl($C_1$–$C_4$)alkyl such as 3-(4-propargylcyclohexyl)propyl.

Halocycloalkylalkyl is, for example, halo($C_3$–$C_6$)cycloalkyl($C_1$–$C_4$)alkyl such as 4-(2,3-dichlorocyclopentyl)butyl.

Alkoxycycloalkylalkyl is, for example, ($C_1$–$C_4$)alkoxy($C_3$–$C_6$)cycloalkyl($C_1$–$C_4$)alkyl such as 4-methoxycyclohexylmethyl.

Alkylene is, for example, a ($C_4$–$C_5$)alkylene such as butylene (—$CH_2CH_2CH_2CH_2$—) and pentylene (—$CH_2CH_2CH_2CH_2CH_2$—).

Alkylthio is, for example, a ($C_1$–$C_4$)alkylthio such as methyl thio, ethylthio and sec-butylthio.

Haloalkylthio is, for example, a halo($C_1$–$C_4$)alkylthio such as chloromethylthio and 3-bromopropylthio.

Alkoxycarbonyl is, for example, a ($C_1$–$C_6$)alkoxycarbonyl such as methoxycarbonyl and n-butoxycarbonyl.

This invention also includes the acid addition salts of the compounds of formula (I) wherein the anionic counterion of the acid is selected in such a manner that the sum of the valence charges of the protonated triazole compound and the anion equals zero.

This invention further includes the metal salt complexes of the compounds of formula (I) wherein the metal is a cation selected from Groups IIA, IVA, IB, IIB, VIB, VIIB and VIII of the Periodic Table and the anionic counterion of the metal is selected in such a manner that the sum of the valence charges of the cation and anion equals zero.

The 1-(disubstituted carbamoyl or thiocarbamoyl)-1,2,4-triazol-3-yl sulfonates and thiosulfonates of this invention can be prepared by conventional synthetic methods. For example, a 1,2,4-triazol-3-yl sulfonate or thiosulfonate of the general formula (II) can be reacted with a carbamoyl or thiocarbamoyl halide of the general formula (III):

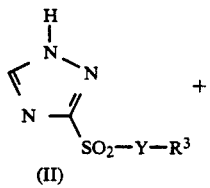

(II)

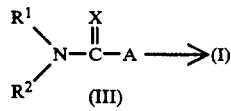

(III)

in which $R^1$, $R^2$, $R^3$, X and Y are as described in Formula (I) and A is chlorine, bromine or fluorine, preferably chlorine. The reaction is suitably effected in an aqueous medium or in the presence of an organic solvent which is inert to the reactants. Such solvents include aromatic hydrocarbons such as toluene or xylene, halogenated hydrocarbons such as methylene chloride or chlorobenzene, ethers such as diethyl ether or tetrahydrofuran, ketones such as acetone or methyl ethyl ketone, organic bases such as pyridine, triethyl amine or N,N-dimethylaniline, acetonitrile, N,N-dimethylformamide and dimethyl sulfoxide. The reaction can be run at a temperature from about the freezing point to the boiling point of the solvent, preferably from about 0° C. to about 150° C., for a time from about 10 minutes to about 48 hours. The reaction is conducted in the presence of an acid acceptor for the hydrogen halide by-product which is generated during the reaction. Examples of such acid acceptors include inorganic bases such as sodium hydroxide, potassium hydroxide, sodium carbonate and sodium bicarbonate or organic bases such as triethyl amine or pyridine. Preferred are the organic bases, such as triethyl amine or pyridine, since they can function as a convenient solvent for the reaction. The usual equivalent ratio of reactants is from about a 1 to 1 ratio of a 1,2,4-triazol-3-yl sulfonate or thiocarbamoyl halide of the general formula (II) to a carbamoyl or thiocarbamoyl halide of the general formula (III) to about a 1 to 1.5 ratio of a 1,2,4-triazol-3-yl sulfonate or thiosulfonate of the general formula (II) to a carbamoyl or thiocarbamoyl halide of the general formula (III). An equivalent ratio of from about a 1 to 1 ratio of compound (II) to the acid acceptor to about a 1 to 10 ratio of compound (II) to the acid acceptor may be conveniently employed. In a slight variation of this procedure, the triazole compound of formula (II) can be reacted with an inorganic base, preferably a Group IA metal hydroxide such as sodium or potassium, and converted to a triazole salt in accordance with known methods prior to the reaction with a carbamoyl halide of formula (III), thus making the use of an acid acceptor unnecessary.

The carbamoyl halides of formula (III) may be prepared by reacting a secondary amine of the formula $R^1NHR^2$, in which $R^1$ and $R^2$ are as described for formula (I), with a carbonyl halide $COA_2$ where A is chlorine, bromine or fluorine, preferably chlorine, in accordance with known methods.

The compounds of formula (I) also can be prepared by a process which comprises reacting a carbamoyl halide of formula (IV) in which $R^3$, X and Y are as described for formula (I) and A as described for formula (III) with a secondary amine of the formula $R^1NHR^2$ in which $R^1$ and $R^2$ are as described for formula (I). The reaction is suitably effected in the presence

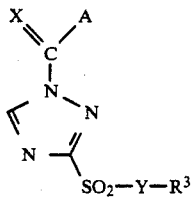

(IV)

of an organic solvent which is inert to the reactants, such as those described for the reaction of compounds of formula (II) with compounds of formula (III). Preferred are the organic bases, such as triethyl amine or pyridine, since they can function as a convenient hydrogen halide acceptor for the reaction.

The carbamoyl halides of formula (IV) can be prepared from triazoles of formula (II) by reaction with a carbonyl halide $COA_2$, preferably phosgene, in accordance with known methods.

The 1,2,4-triazol-3-yl sulfonate or thiosulfonate of the general formula (II) can be prepared by a process which comprises reacting a 1,2,4-triazole-3-sulfonyl halide, preferably the chloride, with a phenol, thiophenol, alcohol or mercaptan of the general formula $R^3YH$ wherein $R^3$ and Y are as described in formula (I). Reaction conditions which are generally employed are the same as those described previously for the reaction of compounds of formula (II) with compounds of formula (III) to produce compounds of formula (I). The 1,2,4-triazole-3-sulfonyl halide can be prepared by halogenating 3-mercapto-1,2,4-triazole in accordance with known methods.

An alternative method for providing compounds of formula (I) is available. For example, a 1-(disubstituted carbamoyl or thiocarbamoyl)-1,2,4-triazole-3-sulfonyl halide of the general formula (V) wherein $R^1$, $R^2$ and X are as described in formula (I) and A is chlorine, bromine or fluorine, preferably chlorine, can be reacted with a phenol, thiophenol, alcohol or mercaptan of the general formula $R^3YH$ wherein $R^3$ and Y are as described in formula (I):

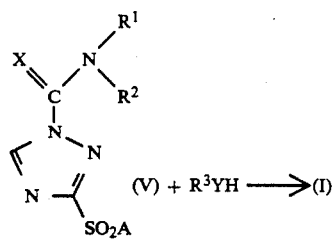

Reaction conditions which are generally employed are those which are utilized for the preparation of intermediates of formula (II). The 1-(disubstituted carbamoyl or thiocarbamoyl)-1,2,4-triazole-3-sulfonyl halides of formula (V) can be prepared by halogenating, preferably chlorinating, a 1-(disubstituted carbamoyl or thiocarbamoyl)-3-[(disubstitued carbamoyl)thio]-1,2,4-triazole of the general formula (VI) wherein $R^1$, $R^2$ and X are as described in formula (I) and A is chlorine, bromine or fluorine, preferably chlorine:

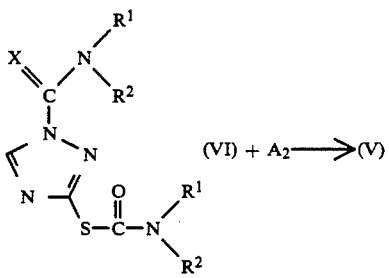

The triazoles of formula (VI) can be conveniently prepared by reaction of 3-mercapto-1,2,4-triazole with a carbamoyl halide of formula (III) in accordance with known methods.

The acid addition salts of the 1,2,4-triazoles of this invention can be prepared by techniques which are well known in the art. A 1,2,4-triazole of formula (I) can be dissolved in an appropriate polar solvent, for example, diethyl ether, tetrahydrofuran, ethanol, methanol or combinations thereof, and reacted at a temperature from about 0° C. to about 50° C. with an equivalent or excess amount of a mineral or organic acid, for example, hydrochloric, sulfuric, nitric, phosphoric and acetic which may or may not be dissolved in a solvent common to the solvent of the triazole solution. The mixture is then either cooled or evaporated to give an acid addition salt of the compounds of formula (I) which can be either used as such or recrystallized from an appropriate solvent or combination of appropriate solvents, for example, methanol, chloroform, acetone, diethyl ether and tetrahydrofuran.

The metal salt complexes of the 1,2,4-triazoles of this invention can be prepared by adding dropwise, with stirring, a stoichiometric amount of a metal salt, for example, zinc (II) chloride and copper (II) chloride, dissolved in an appropriate solvent or combination of solvents to a solution of the 1,2,4-triazole. The reaction mixture is briefly stirred and the solvent is removed, for example, by distillation, to give a metal salt complex of the compounds of formula (I).

An alternative preparation of these metal salt complexes involves mixing stoichiometric or excess amounts of the metal salt and a triazole of formula (I) in a solvent containing adjuvants just prior to spraying the plants. Adjuvants that may be included in this in-situ formulation preparation are detergents, emulsifiers, wetting agents, spreading agents, dispersing agents, stickers and adhesives which are used in agricultural applications.

Solvents that can be utilized in both of these procedures to prepare metal salt complexes include any polar solvent, for example, water, methanol, ethanol, isopropanol or ethylene glycol and any aprotic dipolar solvent, for example, dimethyl sulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead and barium.

Examples of anions that can be used as the counterion in the metal salt include, but are not limited to, chloride, bromide, iodide, sulfate, bisulfate, phosphate, nitrate, perchlorate, carbonate, bicarbonate, hydrosulfide, hydroxide, acetate, oxalate, malate and citrate.

The structures and their melting points (M.P.), when obtained, of typical examples encompassed by the present invention are shown in Tables 1A-1D. Elemental analyses data are provided in Table 2 for those compounds which are oils.

TABLE 1A

Structure and Melting Point of Typical Examples

| Ex. No. | $Z_n$ | M.P. °C. |
|---|---|---|
| 1 | H | 56-57 |
| 3 | 2-Cl | 60-62 |
| 4 | 3-Cl | 110-114 |
| 5 | 4-Cl | 88-92 |
| 6 | 2-$CH_3$ | 54-55 |
| 7 | 3-$CH_3$ | 99-100 |
| 8 | 4-$CH_3$ | 81-83 |
| 9 | 4-$CF_3$ | 87-89 |
| 10 | 4-Br | 88-90 |
| 11 | 4-CN | 106-107 |
| 16 | 4-F | 78-80 |
| 17 | 4-$NO_2$ | 106-108 |
| 18 | 4-$CO_2CH_3$ | 103-105 |
| 19 | 4-$OCH_3$ | 70-72 |
| 20 | 4-$SCH_3$ | 88-89 |
| 21 | 3-$CF_3$ | 74-76 |
| 22 | 4-$CH(CH_3)_2$ | 53-54 |
| 23 | 2-Cl, 3-Cl | 92-95 |
| 24 | 2-Cl, 4-Cl | 88-89 |
| 25 | 3-Cl, 5-Cl | 91-102 |
| 27 | 2-Cl, 5-Cl | 84-86 |
| 28 | 2-Cl, 6-Cl | 87-88 |
| 29 | 3-Cl, 4-Cl | 89-90 |

TABLE 1B

Structure and Melting Point of Typical Examples

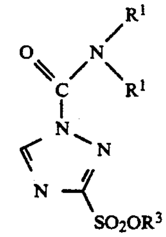

| Ex. No. | $R^1$ | $R^3$ | M.P. °C. |
|---|---|---|---|
| 2 | $C_2H_5$ | $CH_2C(CH_3)_3$ | 51-54 |
| 12 | $C_2H_5$ | $CH_2CHCl_2$ | oil* |
| 13 | $C_2H_5$ | $C_2CCl_3$ | 49-51 |
| 14 | $C_2H_5$ | $CH_2CF_2CF_3$ | oil* |
| 15 | $C_2H_5$ | $CH_2CF_3$ | 41-44 |
| 26 | $C_2H_5$ | $C_2H_5$ | 56-61 |
| 30 | $CH_2CH{=}CH_2$ | $CH_2CF_3$ | 47-48 |
| 32 | $CH_3$ | $CH_2CF_3$ | oil* |
| 33 | $C_2H_5$ | $CH(CH_2F)_2$ | 53-54 |

*Elemental analyses for these compounds are listed in Table 2.

TABLE 1C

Structure and Melting Point of Example 31

M.P. °C. = 102-103

TABLE 1D

Structure and Melting Point of Example 34

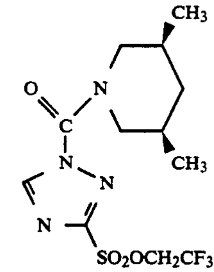

M.P. °C. = 70-71

TABLE 2

Elemental Analyses for Examples 12, 14 and 32

| | Example 12 | | Example 14 | | Example 32 | |
|---|---|---|---|---|---|---|
| Element | Expected | Found | Expected | Found | Expected | Found |
| C | 31.31% | 31.15% | 31.58% | 30.60% | 27.82% | 27.78% |
| H | 4.09% | 4.24% | 3.44% | 3.27% | 3.00% | 2.84% |
| N | 16.23% | 16.24% | 14.73% | 14.72% | 18.54% | 18.56% |
| S | 9.29% | 9.14% | 8.43% | 9.23% | 10.61% | 10.89% |
| Cl | 20.54% | 20.80% | | | | |

EXAMPLE 1

Preparation of Phenyl 1-(N,N-Diethylcarbamoyl)-1,2,4-Triazole-3-Sulfonate a. Preparation of 1,2,4-Triazole-3-Sulfonyl Chloride

To a flask was added 500 milliliters (ml) of 2 molar hydrochloric acid at 0° C. followed by 30.3 grams (g) of 1,2,4-triazole-3-thiol. The resulting solution was vigorously stirred and chlorine gas was passed into it over one hour while maintaining the temperature of the exothermic reaction at 0° C. The solid which formed was filtered off, washed with water at 0° C. and partially dried to yield 26 g of the desired intermediate.

b. Preparation of Phenyl 1,2,4-Triazole-3-Sulfonate

To a flask was added 10 g of thoroughly dried 1,2,4-triazole-3-sulfonyl chloride and 150 ml of tetrahydrofuran. The resulting mixture was stirred under nitrogen until most of the sulfonyl chloride dissolved. Phenol, 6.2 g, was then added at room temperature followed by the slow addition of 9 ml of triethyl amine. A precipitate became apparent and the resulting mixture was stirred for an additional 16 hours. The tetrahydrofuran was evaporated from the mixture and the residue washed with 200 ml of water followed by extraction with 200 ml of ethyl acetate. The ethyl acetate solution was dried using sodium sulfate, filtered and concentrated to yield 10.77 g of the desired intermediate as a white solid.

c. Preparation of Phenyl 1-(N,N-Diethylcarbamoyl)-1,2,4-Triazole-3-Sulfonate To a flask was added 9.76 g of phenyl 1,2,4-triazole-3sulfonate and 40 ml of dry pyridine. The mixture was stirred under nitrogen until a solution became apparent. Diethylcarbamoyl chloride, 5.6 ml, was then added and the resulting mixture stirred under nitrogen at room temperature for 16 hours. The mixture was then poured into 100 ml of 2N hydrochloric acid and extracted twice with 100 ml portions of ethyl acetate. The ethyl acetate solution was dried using sodium sulfate, filtered and concentrated to yield 11.12 g of the desired product as a white solid.

Using the procedures of Example 1 except for the substitution of the indicated substituted phenol or alcohol for phenol in Example 1b, the following Examples were prepared:

| EXAMPLE NO. | Phenol or Alcohol Used in 1b |
| --- | --- |
| 2 | neopentyl alcohol |
| 3 | 2-chlorophenol |
| 4 | 3-chlorophenol |
| 5 | 4-chlorophenol |
| 6 | 2-methylphenol |
| 7 | 3-methylphenol |
| 8 | 4-methylphenol |
| 9 | 4-(trifluoromethyl)phenol |
| 10 | 4-bromophenol |
| 11 | 4-cyanophenol |
| 12 | 2,2-dichloroethanol |
| 13 | 2,2,2-trichloroethanol |
| 14 | 2,2,3,3,3-pentafluoropropanol |
| 15 | 2,2,2-trifluoroethanol |
| 16 | 4-fluorophenol |
| 17 | 4-nitrophenol |
| 18 | methyl 4-hydroxybenzoate |
| 19 | 4-methoxyphenol |
| 20 | 4-(methylthio)phenol |
| 21 | 3-(trifluoromethyl)phenol |
| 22 | 4-isopropylphenol |
| 23 | 2,3-dichlorophenol |
| 24 | 2,4-dichlorophenol |
| 25 | 3,5-dichlorophenol |
| 27 | 2,5-dichlorophenol |
| 28 | 2,6-dichlorophenol |
| 29 | 3,4-dichlorophenol |
| 33 | 1,3-difluoro-2-propanol |

Using the procedures of Example 1 except for the substitution of 2,2,2-trifluoroethanol for phenol in Example 1b and the indicated carbamoyl chloride for diethylcarbamoyl chloride in Example 1c, the following Examples were prepared:

| EXAMPLE NO. | Carbamoyl Chloride Used in 1c |
| --- | --- |
| 30 | diallylcarbamoyl chloride |
| 31 | dimethylthiocarbamoyl chloride |
| 32 | dimethylcarbamoyl chloride |
| 34 | cis-3,5-dimethylpiperidinylcarbamoyl chloride |

EXAMPLE 26

Preparation of Ethyl 1-(N,N-Diethylcarbamoyl)-1,2,4-Triazole-3-Sulfonate a. Preparation of 1-(N,N-Diethylcarbamoyl)-3-[(N,N-Diethylcarbamoyl)thio]-1,2,4-Triazole To a flask was added 17.17 g of 1,2,4-triazole-3-thiol and 200 ml of dry tetrahydrofuran. The mixture was stirred under nitrogen at room temperature and 43 ml of diethylcarbamoyl chloride was quickly added dropwise. The mixture was cooled to between 0° C. and 5° C. Dimethylaminopyridine, one gram, was added followed by the slow dropwise addition of 47.4 ml of triethyl amine while maintaining the reaction temperature between 0° C. and 5° C. until all the triethyl amine was added. The mixture became thick and was allowed to warm to room temperature, then was refluxed at 70° C. for about 20 minutes. After the mixture was cooled to room temperature, the volatiles were evaporated off to leave an oily residue. Water, 100 ml, was added to the residue which was then extracted twice with 100 ml portions of ethyl acetate. The ethyl acetate layer was dried using magnesium sulfate and concentrated to a pale yellow solid which was dried thoroughly under vacuum to yield 31.03 g of pale yellow solid.

b. Preparation of 1-(N,N-Diethylcarbamoyl)-1,2,4-Triazole-3-Sulfonyl Chloride To a flask was added 50 g of 1-N,N-diethylcarbamoyl)-3-[(N,N-diethylcarbamoyl)thio]-1,2,4-triazole followed by 500 ml of 2N hydrochloric acid. Chlorine was passed through the vigorously stirred mixture for 20 minutes at a temperature of from 0° C. to 5° C. The quickly completed reaction was allowed to warm to room temperature and filtered to obtain a white solid. After drying thoroughly for about 16 hours, 23.84 g of the desired intermediate was obtained.

c. Preparation of 2,2,2-Trifluoroethyl 1-(N,N-Diethylcarbamoyl)-1,2,4-Triazole-3-Sulfonate This example was prepared using the procedure of Example 1b except for the substitution of 1-(N,N-diethylcarbamoyl)-1,2,4-triazole-3-sulfonyl chloride for 1,2,4-triazole-3-sulfonyl chloride and 2,2,2trifluoroethanol for phenol.

The following test procedure was employed to assess the herbicidal activity of the compounds of the invention.

Seeds of selected plants were planted in flats or pots. For pre-emergence tests, immediately after planting, the test compound was sprayed directly onto the soil surface. The flats or pots were then placed in a greenhouse and watered. For postemergence tests, the seeds were allowed to germinate and grow in a greenhouse for 10 to 21 days. Before application, each series of test plants were selected for uniformity, size and stage of development. The test plants were then treated with the test compound. The plants for postemergence tests were returned to the greenhouse and then watered. Test species employed were:

| | MONOCOTS | |
|---|---|---|
| CODE | COMMON NAME | SCIENTIFIC NAME |
| BYG | Barnyardgrass | Echinochloa crus-galli |
| FOX | Green Foxtail | Setaria viridis |
| JON | Johnsongrass | Sorghum halepense |
| NUT | Nutsedge | Cyperus esculentus |

| | MONOCOTS | |
|---|---|---|
| CODE | COMMON NAME | SCIENTIFIC NAME |
| WO | Wild Oat | Avena fatua |

| | DICOTS | |
|---|---|---|
| CODE | COMMON NAME | SCIENTIFIC NAME |
| CKL | Cocklebur | Xanthium strumarium |
| MG | Morningglory | Ipomoea lacunosa |
| PIG | Pigweed | Amaranthus retroflexus |
| SMT | Smartweed | Polygonum lapathifolium |
| VEL | Velvetleaf | Abutilon theophrasti |

The compound to be evaluated was dissolved in an appropriate solvent, usually acetone, and sprayed over the flats or pots using a carrier volume equivalent to 25 or 50 gallons per acre at a rate of application of two (2) pounds per acre (lb/A). About two or three weeks after application of the test compound, the state of growth of the plants was observed. Each species was evaluated on a scale of 0–100 in which 0 equals no activity and 100 equals total control.

The results are shown in Table 2.

TABLE 2

Herbicidal Test Data for Examples 1–34

| Ex. No. | Appl. Type | CKL | MG | PIG | SMT | VEL | BYG | FOX | JON | NUT | WO |
|---|---|---|---|---|---|---|---|---|---|---|---|
| 1. | Pre | 0 | 0 | 100 | 100 | 0 | 100 | 100 | 100 | —* | 100 |
|  | Post | 15 | 0 | 0 | 0 | 0 | 15 | 25 | 0 | 0 | 0 |
| 2. | Pre | 0 | 0 | 0 | 0 | 0 | 60 | 100 | 15 | 0 | 0 |
|  | Post | 0 | 0 | 0 | 0 | 0 | 45 | 10 | 0 | 0 | 0 |
| 3. | Pre | 0 | 0 | 100 | 60 | 0 | 100 | 100 | 15 | 15 | 21 |
|  | Post | 0 | 0 | 0 | 0 | 0 | 5 | 0 | 0 | 0 | 0 |
| 4. | Pre | 0 | 0 | 100 | 0 | 0 | 100 | 100 | 15 | 5 | 71 |
|  | Post | 0 | 10 | 0 | 0 | 0 | 10 | 15 | 0 | 0 | 0 |
| 5. | Pre | 0 | 0 | 100 | 100 | 0 | 100 | 100 | 35 | 10 | 41 |
|  | Post | 0 | 0 | 0 | 0 | 0 | 25 | 30 | 0 | 0 | 10 |
| 6. | Pre | 0 | 0 | 100 | 0 | 0 | 100 | 100 | 31 | 16 | 31 |
|  | Post | 15 | 0 | 0 | 10 | 0 | 10 | 10 | 0 | 0 | 5 |
| 7. | Pre | 0 | 0 | 100 | 100 | 0 | 100 | 100 | 100 | 10 | 90 |
|  | Post | 0 | 5 | 10 | 0 | 0 | 0 | 0 | 0 | 0 | 0 |
| 8. | Pre | 0 | 0 | 100 | 100 | 0 | 100 | 100 | 35 | 0 | 41 |
|  | Post | 0 | 0 | 0 | 0 | 0 | 0 | 0 | 0 | 0 | 0 |
| 9. | Pre | 0 | 0 | 100 | —* | —* | 100 | 100 | 100 | 100 | 56 |
|  | Post | 20 | 10 | 0 | 35 | 35 | 20 | 0 | 51 | 0 | 0 |
| 10. | Pre | 0 | 0 | 100 | —* | 0 | 100 | 100 | 66 | 0 | 26 |
|  | Post | 0 | 0 | 0 | 0 | 0 | 0 | 16 | 61 | 0 | 0 |
| 11. | Pre | 0 | 0 | 100 | —* | 0 | 100 | 100 | 31 | 100 | 0 |
|  | Post | 0 | 0 | 0 | 0 | 0 | 0 | 0 | 0 | 0 | 0 |
| 12. | Pre | 0 | 0 | 100 | 71 | 25 | 66 | 15 | 90 | —* | 100 |
|  | Post | 0 | 15 | 90 | —* | 10 | 76 | 35 | 0 | 0 | 0 |
| 13. | Pre | 0 | 0 | 100 | 0 | 0 | 86 | 100 | 100 | —* | 81 |
|  | Post | 0 | 10 | 0 | —* | 0 | 0 | 15 | 0 | 0 | 0 |
| 14. | Pre | 0 | 0 | 100 | 0 | 25 | 100 | 100 | 100 | —* | 95 |
|  | Post | 0 | 76 | 0 | —* | 26 | 16 | 10 | 11 | 0 | 0 |
| 15. | Pre | 0 | 10 | 100 | 100 | 100 | 100 | 100 | 100 | 46 | 100 |
|  | Post | 0 | 63 | 13 | 5 | 20 | 58 | 33 | 8 | 50 | 40 |
| 16. | Pre | 0 | 0 | 100 | 100 | 0 | 100 | 100 | 100 | —* | 80 |
|  | Post | 0 | 15 | 60 | 20 | 0 | 25 | 10 | 25 | 0 | 41 |
| 17. | Pre | 0 | —* | 100 | 0 | 0 | 100 | 100 | 0 | 0 | 0 |
|  | Post | 0 | 10 | 0 | 0 | 0 | 0 | 0 | 0 | 0 | 0 |
| 18. | Pre | 0 | 0 | 100 | 0 | 0 | 45 | 0 | 0 | 0 | 0 |
|  | Post | 0 | 10 | 0 | 0 | 0 | 0 | 0 | 0 | 0 | 31 |
| 19. | Pre | 0 | 0 | 100 | 100 | 0 | 100 | 100 | 0 | 0 | 81 |
|  | Post | 0 | 5 | 0 | 0 | 0 | 0 | 0 | 21 | 0 | 31 |
| 20. | Pre | 0 | 0 | 100 | 0 | 0 | 95 | 98 | 0 | 16 | 81 |
|  | Post | 0 | 80 | 35 | 75 | 21 | 31 | 71 | 0 | —* | 50 |
| 21. | Pre | 0 | 0 | 100 | 25 | 0 | 95 | 80 | 21 | 0 | 91 |
|  | Post | 0 | 20 | 10 | 80 | 11 | 21 | 81 | 0 | —* | 65 |
| 22. | Pre | 0 | 0 | 100 | 0 | 0 | 95 | 99 | 65 | 0 | 81 |
|  | Post | 0 | 90 | 0 | 25 | 21 | 51 | 41 | 0 | —* | 20 |
| 23. | Pre | 0 | 0 | 100 | 100 | 20 | 100 | 90 | 21 | 0 | 61 |
|  | Post | 0 | 10 | 0 | 0 | 0 | 0 | 0 | 0 | 0 | 0 |
| 24. | Pre | 0 | 0 | 100 | 0 | 0 | 100 | 95 | 21 | 0 | 11 |

TABLE 2-continued
Herbicidal Test Data for Examples 1-34

| Ex. No. | Appl. Type | CKL | MG | PIG | SMT | VEL | BYG | FOX | JON | NUT | WO |
|---|---|---|---|---|---|---|---|---|---|---|---|
| | Post | 0 | 20 | 0 | 0 | 0 | 36 | 0 | 0 | 0 | 0 |
| 25. | Pre | 0 | 0 | 100 | 0 | 0 | 100 | 100 | 61 | —* | 31 |
| | Post | 0 | 10 | 0 | 0 | 0 | 0 | 0 | 0 | 0 | 0 |
| 26. | Pre | 0 | 0 | 0 | 0 | 0 | 91 | 100 | 51 | 0 | 11 |
| | Post | 0 | 0 | 0 | 0 | 0 | 0 | 0 | 0 | 0 | 0 |
| 27. | Pre | —* | 0 | 100 | 0 | 0 | 100 | 100 | 21 | —* | 11 |
| | Post | 0 | 16 | 0 | 0 | 0 | 0 | 0 | 0 | 0 | 0 |
| 28. | Pre | 0 | 60 | 0 | 0 | 0 | 100 | 55 | 71 | —* | 11 |
| | Post | 0 | 10 | 0 | 0 | 0 | 0 | 0 | 0 | 0 | 0 |
| 29. | Pre | 0 | 0 | 100 | 100 | 0 | 71 | 86 | 21 | 0 | 21 |
| | Post | 0 | 20 | 0 | 15 | 0 | 0 | 0 | 0 | 0 | 0 |
| 30. | Pre | 0 | 0 | 90 | 100 | 0 | 88 | 100 | 56 | 0 | 0 |
| | Post | 5 | 35 | 12 | 5 | 10 | 5 | 2 | 0 | 0 | 0 |
| 31. | Pre | 0 | 0 | 0 | 50 | 0 | 0 | 0 | 0 | 0 | 0 |
| | Post | 0 | 2 | 0 | 0 | 0 | 0 | 8 | 0 | 0 | 0 |
| 32. | Pre | 0 | 0 | 0 | 0 | 0 | 10 | 0 | 43 | 0 | 0 |
| | Post | 0 | 35 | 8 | 0 | 5 | 0 | 0 | 2 | 0 | 0 |
| 33. | Pre | 21 | 0 | 100 | 100 | 90 | 100 | 100 | 90 | 15 | 81 |
| | Post | 0 | 75 | 5 | 0 | 15 | 76 | 46 | 0 | 15 | 61 |
| 34. | Pre | 0 | 0 | 100 | 100 | 0 | 91 | 25 | 21 | 0 | 21 |
| | Post | 0 | 15 | 0 | 0 | 0 | 0 | 0 | 0 | 0 | 0 |

*Not Tested

The compounds of this invention are active herbicidally on monocot and dicot weeds in either pre- or postemergence applications. In general, they require lower doses to control monocot weeds preemergence. In particular, several annular grasses, such as Echinochloa crus-galli, Setaria viridis and Sorghum halepense are especially sensitive. The compounds of this invention generally show selectivity to several agronomically important crops such as corn, soybeans, wheat, rice, cotton and sugarbeets. The compounds of this invention also possess utility for non-selective uses.

The invention is most effective when the compounds are formulated in an appropriate carrier, such that the dissolved or dispersed compound is readily applied over the plants or soil in a uniform manner.

The invention is also effective when used as a part of a mixture of herbicides formulated in the above manner.

The present herbicides may be applied in any amount which will give the required control of the undesired plants. Generally a rate of application of the herbicides of the invention is from about 0.001 to about 8 pounds per acre and preferably from about 0.01 to about 4 pounds of the compound per acre. Most preferably a rate from about 0.1 to about 2 pounds per acre is used.

The compounds of the present invention are useful both as preemergence and postemergence herbicides. Preemergence herbicides may be applied to the soil surface or incorporated into the soil. Postemergence herbicides are those which are applied after the plants have emerged and during their growth period. The compounds of the present invention may be applied to the soil surface prior to plant emergence or incorporated into the soil or other growth medium prior to planting. This incorporation can be carried out by any convenient means, including by simply mixing with the soil, by applying the compound to the surface of the soil and then disking or dragging into the soil to the desired depth, or by employing a liquid carrier to accomplish the necessary penetration and impregnation.

A compound of the present invention can be applied postemergence to the growth medium or to plants to be treated either by itself, or, as is generally done, as a component in a herbicidal composition or formulation which also comprises an agronomically acceptable carrier.

By agronomically acceptable carrier is meant any substance which can be used to dissolve, disperse or diffuse a herbicidal compound in the composition without impairing the effectiveness of the herbicidal compound and which by itself has no detrimental effect on the soil, equipment, crops or agronomic environment. Mixtures of the compounds of the present invention may also be used in any of these herbicidal formulations. The herbicidal compositions of the invention can be either solid or liquid formulations or solutions. For example, the compounds can be formulated as wettable powders, solutions, emulsifiable concentrates, dusts, granular formulations, aerosols, water dispersable granular formulations or flowable concentrates as is known to one in the art. In such formulations, the compounds are extended with a liquid or solid carrier and, when desired, suitable surfactants or emulsifiers are incorporated.

It is usually desirable, particularly in postemergence applications, to include adjuvants such as wetting agents, spreading agents, dispersing agents, sticking agents, adhesives and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide and the like. Mixtures of these solvents can also be used. The concentration of compound in the solution can vary from about 2% to about 98%.

The compounds of the present invention can also be mixed with fertilizers or fertilizing materials before their application. In one type of solid fertilizing composition in which the compounds may be used, particles of a fertilizer or fertilizing ingredients, such as ammonium sulfate, ammonium nitrate or ammonium phosphate can be coated with one or more of the herbicides. The solid herbicide and solid fertilizing material may also be admixed in blending or mixing equipment, or they can be incorporated with fertilizers in granular formulations. Any relative proportion of herbicide and fertilizer can be used which is suitable for the crops and weeds to be treated.

The compounds of the present invention may be applied as herbicidal sprays by methods commonly employed, such as conventional high-gallonage hydraulic sprays, low gallonage sprays, air blast spray, aerial sprays and dusts. For some applications, two or more of the compounds of the instant invention may be combined, thereby providing additional advantages and effectiveness. When mixtures of the compounds of the invention are used, the relative proportion of each compound used will depend on the relative efficacy of the compounds in the mixture with respect to the plants to be treated.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

Carboxylic Acids and Derivatives 2,3,6-trichlorobenzoic acid and its salts; 2,3,5,6-tetrachlorobenzoic acid and its salts; 2-methoxy-3,5,6-trichlorobenzoic acid and its salts; 2-methoxy-3,6-dichlorobenzoic acid and its salts; 2-methyl-3,6-dichlorobenzoic acid and its salts; 2,3-dichloro-6-methylbenzoic acid and its salts; 2,4-dichlorophenoxyacetic acid and its salts and esters; 2,4,5-trichlorophenoxyacetic acid and its salts and esters; 2-methyl-4-chlorophenoxyacetic acid and its salts and esters; 2-(2,4,5-trichlorophenoxy)propionic acid and its salts and esters; 4-(2,4-dichlorophenoxy)butyric acid and its salts and esters; 4-(2-methyl-4-chlorophenoxy)butyric acid and its salts and esters; 2,3,6-trichlorophenylacetic acid and its salts; 3,6-endoxohexahydrophthalic acid and its salts; dimethyl 2,3,5,6-tetrachloroterephthalate; trichloroacetic acid and its salts; 2,2-dichloropropionic acid and its salts; 2,3-dichloroisobutyric acid and its salts; isopropylammonium 2-(4-isopropyl-5-methyl-5-oxo-2-imidazolin-2-yl)nicotinate; 2-[4,5-dihydro-4-methyl-4-(1-methylethyl)-5-oxo-1H-imidazol-2-yl]-3-quinolinecarboxylic acid; m-toluic acid, 6-(4-isopropyl-4-methyl-5-oxo-2-imidazolin-2-yl)-, methyl ester and p-toluic acid, 6-(4-isopropyl-4-methyl-5-oxo-2-imidazolin-2-yl)-, methyl ester; N-(phosphomethyl)glycine isopropylammonium salt; [3,5,6-trichloro-(2-pyridinyl)oxy]acetic acid; 3,7-dichloro-8-quinolinecarboxylic acid; ammonium DL-homoalanin-4-yl(methyl)phosphinate.

Carbamic Acid Derivatives ethyl N,N-di(n-propyl)thiolcarbamate; n-propyl N,N-di(n-propyl)thiolcarbamate; ethyl N-ethyl-N-(n-butyl)thiolcarbamate; n-propyl N-ethyl-N-(n-butyl)thiolcarbamate; 2-chloroallyl N,N-diethyldithiocarbamate; isopropyl N-phenylcarbamate; isopropyl N-(m-chlorophenyl)carbamate; 4-chloro-2-butynyl-N-(m-chlorophenyl)carbamate; methyl N-(3,4-dichlorophenyl)carbamate; dinitro-o-(sec-butyl)phenol and its salts; pentachlorophenol and its salts; S-(4-chlorobenzyl)-N,N-diethylthiolcarbamate.

Ureas 2-chloro-N-[(4-methoxy-6-methyl-1,3,5-triazin-2-yl)aminocarbonyl]-benzenesulfonamide; 3-(3,4-dichlorophenyl)-1,1-dimethylurea; 3-phenyl-1,1-dimethylurea; 3-(3,4-dichlorophenyl)-3-methoxy-1,1-dimethylurea; 3-(4-chlorophenyl)-3-methoxy-1,1-dimethylurea; 3-(3,4-dichlorophenyl)-1-n-butyl-1-methylurea; 3-(3,4-dichlorophenyl)-1-methoxy-1-methylurea; 3-(4-chlorophenyl)-1-methoxy-1-methylurea; 3-(3,4-dichlorophenyl)-1,1,3-trimethylurea; 3-(3,4-dichlorophenyl)diethylurea; dichloral urea; methyl 2-[[[[(4,6-dimethyl-2-pyrimidinyl)amino]carbonyl]amino]sulfonyl]-benzoate; N-((6-methoxy-4-methyl-1,3,5-triazin-2-yl)aminocarbonyl)-2-(2-chloroethoxy)benzenesulfonamide; 2-[[[(4-chloro-6-methoxypyrimidine-2-yl)aminocarbonyl]amino]sulfonyl]benzoic acid, ethyl ester; methyl 2-[[[[(4-methoxy-6-methyl-1,3,5-triazin-2-yl)amino]carbonyl]amino]sulfonyl]-benzoate; methyl 3-[[(4-methoxy-6-methyl-1,3,5-triazin-2-yl)aminocarbonyl]aminosulfonyl]-2-thiophenecarboxylate; methyl 2-[[[[(4,6-dimethoxypyrimidin-2-yl)amino]carbonyl]amino]sulfonyl]methyl]benzoate; methyl 2-[[[[(4-methoxy-6-methyl-1,3,5-triazin-2-yl)methylamino]carbonyl]amino]sulfonyl]benzoate.

Substituted Triazines 2-chloro-4,6-bis(ethylamino)-s-triazine; 2-chloro-4-ethylamino-6-isopropylamino-s-triazine; 2-chloro-4,6-bis(methoxy-n-propylamino)-s-triazine; 2-methoxy-4,6-bis(isopropylamino)-s-triazine; 2-chloro-4-ethylamino-6-(3-methoxy-n-propylamino)-s-triazine; 2-methylmercapto-4,6-bis(isopropylamino)-s-triazine; 2-methylmercapto-4,6-bis(ethylamino)-2-triazine; 2-methylmercapto-4-ethylamino-6-isopropylamino-s-triazine; 2-chloro-4,6-bis(isopropylamino)-s-triazine; 2-methoxy-4-ethylamino-6-isopropylamino-s-triazine; 2-methylmercapto-4-(2-methoxyethylamino)-6-isopropylamino-s-triazine; 4-amino-6-(t-butyl)-3-(methylthio)-1,2,4-triazine-5(4H)-one.

Diphenyl Ether Derivatives 2,4-dichloro-4'-nitrodiphenyl ether; 2,4,6-trichloro-4'-nitrodiphenyl ether; 2,4-dichloro-6-fluoro-4'-nitrodiphenyl ether; 3-methyl-4'-nitrodiphenyl ether; 3,5-dimethyl-5'-nitrodiphenyl ether; 2,4'-dinitro-4-(trifluoromethyl)diphenyl ether; 2,4-dichloro-3'-methoxy-4'-nitrodiphenyl ether; sodium 5-(2-chloro-4-(trifluoromethyl)phenoxy)-2-nitrobenzoate; 2-chloro-1-(3-ethoxy-4-nitrophenoxy)-4-(trifluoromethyl)benzene; 1-(carboethoxy)ethyl 5-[2-chloro-4-(trifluoromethyl)phenoxy]-2-nitrobenzoate; 5-[2-chloro-4-(trifluoromethyl)phenoxy]-N-(methylsulphonyl)-2-nitrobenzamide.

Anilides 2-chloro-N-(2-ethyl-6-methylphenyl)-N-(2-methoxy-1-methylethyl)acetamide; 2-chloro-2',6'-diethyl-N-(2-propyloxyethyl)acetanilide; N-(3,4-dichlorophenyl)-propionamide; N-(3,4-dichlorophenyl)methacrylamide; N-(3-chloro-4-methylphenyl)-2-methylpentanamide; N-(3,4-dichlorophenyl)trimethylacetamide; N-(3,4-dichlorophenyl)-alpha,alpha-dimethylvaleramide; N-isopropyl-N-phenylchloroacetamide; N-n-butoxymethyl-N-(2,6-diethylphenyl)chloroacetamide; N-methoxymethyl-N-(2,6-diethylphenyl)chloroacetamide.

Oxyphenoxy Herbicides 2-(4-(2,4-dichlorophenoxy)phenoxy)methyl propionate; methyl 2-(4-(3-chloro-5-(trifluoromethyl)-2-pyridinyloxy)phenoxy)propanoate; butyl (R)-2-[4-[5-(trifluoromethyl)-2-pyridinyloxy]phenoxy]propionate; ethyl 2-[4-[(6-chloro-2-benzoxazolyl)oxy]phenoxy]propanoate; butyl 2-[4-[[5-(trifluoromethyl)-2-pyridinyl]oxy]phenoxy]propionate; 2-[4-[(6-chloro-2-quinoxalinyl)oxy]phenoxy]propionic acid, ethyl ester.

Uracils 5-bromo-3-sec-butyl-6-methyluracil; 5-bromo-3-cyclohexyl-1,6-dimethyluracil; 3-cyclohexyl-5,6-trimethyleneuracil; 5-bromo-3-isopropyl-6-methyluracil; 3-tert-butyl-5-chloro-6-methyluracil.

Nitriles 2,6-dichlorobenzonitrile; diphenylacetonitrile; 3,5-dibromo-4-hydroxybenzonitrile; 3,5-diiodo-4-hydroxybenzonitrile.

Other Organic Herbicides 2-chloro-N,N-diallylacetamide; N-(1,1-dimethyl-2-propynyl)-3,5-dichlorobenzamide; maleic hydrazide; 3-amino-1,2,4-triazole; monosodium methanearsonate; disodium methanearsonate; N,N-dimethyl-alpha,alpha-diphenylacetamide; N-N-di(n-propyl)-2,6-dinitro-4-(trifluoromethyl)aniline; N,N-di(n-propyl)-2,6-dinitro-4-methylaniline; N,N-di(n-propyl)-2,6-dinitro-4-methylsulfonylaniline; O-(2,4-dichlorophenyl)-O-methyl isopropylphosphoramidothioate; 4-amino-3,5,6-trichloropicolinic acid; 2,3-dichloro-1,4-naphthoquinone; di(methoxythiocarbonyl)disulfide; 3-(1-methylethyl)-1H-2,1,3-benzothiadiazin-(4)3H-one-2,2-dioxide; 6,7-dihydrodipyridol[1,2-a:2',1'-c]pyrazidiium salts; 1,1'-dimethyl-4,4'-bipyridinium salts; 3,4,5,6-tetrahydro-3,5-dimethyl-2-thio-2H-1,3,5-thiadiazine; 2-[1-(ethoxyimino)butyl]-5-[s-(ethylthio)propyl]-3-hydroxy-2-cyclohexen-1-one; 2-(2-chlorophenyl)methyl-4,4-dimethyl-3-isoxazolidinone; N-(1-ethylpropyl)-3,4-dimethyl-2,6-dinitrobenzamide; 4-chloro-5-(methylamino)-2-(α,α,α-trifluoro-m-toluyl)-3-(2H)-pyridazinone; 2-(3,5-dichlorophenyl)-2-(2,2,2-trichloromethyl)oxirane; N,N-di(n-propyl)-2,6-dinitro-4-methylaniline; N,N-di(n-propyl)-2,6-dinitro-4-methylsulfonylaniline; O-(2,4-dichlorophenyl)-O-methyl isopropylphosphoramidothioate; 4-amino-3,5,6-trichloropicolinic acid; 2,3-dichloro-1,4-naphthoquinone; di(methoxythiocarbonyl)disulfide; 3-(1-methylethyl)-1H-2,1,3-benzothiadiazin-(4)3H-one-2,2-dioxide; 6,7-dihydrodipyridol[1,2-a:2',1'-c]pyrazidiium salts; 1,1'-dimethyl-4,4'-bipyridinium salts; 3,4,5,6-tetrahydro-3,5-dimethyl-2-thio-2H-1,3,5-thiadiazine; 2-[1-(ethoxyimino)butyl]-5-[s-(ethylthio)propyl]-3-hydroxy-2-cyclohexen-1-one; 2-(2-chlorophenyl)methyl-4,4-dimethyl-3-isoxazolidinone; N-(1-ethylpropyl)-3,4-dimethyl-2,6-dinitrobenzamide; 4-chloro-5-(methylamino)-2-(α,α,α-trifluoro-m-toluyl)-3-(2H)-pyridazinone; 2-(3,5-dichlorophenyl)-2-(2,2,2-trichloromethyl)oxirane.

I claim:

1. A compound of the formula

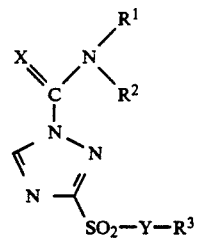

wherein $R^1$ and $R^2$ are each independently selected from the group consisting of alkyl, alkenyl, alkynyl, cycloalkyl, cycloalkenyl, alkylcycloalkyl, alkenylcycloalkyl, alkynylcycloalkyl, haloalkyl, haloalkenyl, haloalkynyl, halocycloalkyl, alkoxyalkyl, alkoxyalkenyl, alkoxyalkynyl, alkoxycycloalkyl, haloalkoxyalkyl, haloalkoxyalkenyl, haloalkoxyalkynyl, haloalkoxycycloalkyl, cycloalkylalkyl, cycloalkenylalkyl, alkylcycloalkylalkyl, alkenylcycloalkylalkyl, alkynylcycloalkylalkyl, halocycloalkylalkyl and alkoxycycloalkylalkyl, or $R^1$ and $R^2$ may together represent a $(C_4-C_5)$alkylene group or a $(C_4-C_5)$alkylene group substituted with one or two substituents each independently selected from the group consisting of alkyl, alkenyl, alkynyl, cycloalkyl, alkoxy, halo and haloalkoxy, so as to form a nitrogen-containing five or six membered cyclic ring with the nitrogen to which they attach, $R^3$ is alkyl, haloalkyl, cycloalkyl, halocycloalkyl, alkenyl, cycloalkylalkenyl, alkoxyalkenyl, haloalkenyl, cycloalkenyl, halocycloalkenyl, aryl, aralkyl, or aryl or aralkyl both substituted on the aryl ring with one to three substituents each independently selected from the group consisting of alkyl, alkenyl, alkynyl, cycloalkyl, halo, haloalkyl, alkoxy, haloalkoxy, cyano, nitro, alkoxycarbonyl, alkylthio and haloalkylthio, X and Y are each independently oxygen (O) or sulfur (S), or the agronomically acceptable acid addition salts and metal complexes thereof.

2. The compound of claim 1 wherein $R^1$ and $R^2$ are each independently selected from the group consisting of $(C_1-C_6)$alkyl, $(C_2-C_4)$alkenyl, $(C_2-C_4)$alkynyl, $(C_3-C_6)$cycloalkyl, $(C_5-C_6)$cycloalkenyl, $(C_1-C_3)$alkyl$(C_3-C_6)$cycloalkyl, $(C_2-C_3)$alkenyl$(C_3-C_6)$cycloalkyl, $(C_2-C_3)$alkynyl$(C_3-C_6)$cycloalkyl, halo$(C_1-C_4)$alkyl, halo$(C_2-C_4)$alkenyl, halo$(C_2-C_4)$alkynyl, halo$(C_3-C_6)$cycloalkyl, $(C_1-C_4)$alkoxy$(C_1-C_6)$alkyl, $(C_1-C_4)$alkoxy$(C_2-C_4)$alkenyl, $(C_1-C_4)$alkoxy$(C_2-C_4)$alkynyl, $(C_1-C_4)$alkoxy$(C_3-C_6)$cycloalkyl, halo$(C_1-C_4)$alkoxy$(C_1-C_6)$alkyl, halo$(C_1-C_4)$alkoxy$(C_2-C_4)$alkenyl, halo$(C_1-C_4)$alkoxy$(C_2-C_4)$alkynyl, halo$(C_1-C_4)$alkoxy$(C_3-C_6)$cycloalkyl, $(C_3-C_6)$cycloalkyl$(C_1-C_4)$alkyl, $(C_5-C_6)$cycloalkenyl$(C_1-C_4)$alkyl, $(C_1-C_4)$alkyl$(C_3-C_6)$cycloalkyl$(C_1-C_4)$alkyl, $(C_2-C_4)$alkenyl$(C_3-C_6)$cycloalkyl$(C_1-C_4)$alkyl, $(C_2-C_4)$alkynyl$(C_3-C_6)$cycloalkyl$(C_1-C_4)$alkyl, halo$(C_3-C_6)$cycloalkyl$(C_1-C_4)$alkyl and $(C_1-C_4)$alkoxy$(C_3-C_6)$cycloalkyl$(C_1-C_4)$alkyl, or $R^1$ and $R^2$ may together represent a $(C_4-C_5)$alkylene group or a $(C_4-C_5)$alkylene group substituted with one or two substituents each independently selected from the group consisting of ($C_1$-$C_4$)alkyl, ($C_2$-$C_4$)alkenyl, ($C_2$-$C_4$)alkynyl, ($C_3$-$C_6$)cycloalkyl, ($C_1$-$C_4$)alkoxy, halo and halo($C_1$-$C_4$)alkoxy, so as to form a nitrogen-containing five or six membered cyclic ring with the nitrogen to which they attach, $R^3$ is ($C_1$-$C_8$)alkyl, halo($C_1$-$C_4$)alkyl, ($C_3$-$C_6$)cycloalkyl, halo($C_3$-$C_6$)cycloalkyl, ($C_2$-$C_4$)alkenyl, ($C_3$-$C_6$)cycloalkyl($C_2$-$C_4$)alkenyl, ($C_1$-$C_4$)alkoxy($C_2$-$C_4$)alkenyl, halo($C_2$-$C_4$)alkenyl, ($C_3$-$C_6$)cycloalkenyl, halo($C_3$-$C_6$)cycloalkenyl, ($C_6$-$C_{10}$)aryl, ($C_6$-$C_{10}$)ar($C_1$-$C_6$)alkyl, or ($C_6$-$C_{10}$)aryl or ($C_6$-$C_{10}$)ar($C_1$-$C_6$)alkyl both substituted on the aryl ring with one to three substituents each independently selected from the group consisting of ($C_1$-$C_6$)alkyl, ($C_2$-$C_4$)alkenyl, ($C_2$-$C_4$)alkynyl, ($C_3$-$C_6$)cycloalkyl, halo, halo($C_1$-$C_4$)alkyl, ($C_1$-$C_4$)alkoxy, halo($C_1$-$C_4$)alkoxy, cyano, nitro, ($C_1$-$C_6$)alkoxycarbonyl, ($C_1$-$C_4$)alkylthio and halo($C_1$-$C_4$)alkylthio, X and Y are each independently oxygen (O) or sulfur (S), or the agronomically acceptable acid addition salts and metal complexes thereof.

3. The compound of claim 2 wherein $R^1$ and $R^2$ are each independently selected from the group consisting of ($C_1$-$C_4$)alkyl, ($C_2$-$C_4$)alkenyl, ($C_2$-$C_4$)alkynyl, ($C_5$-$C_6$)cycloalkyl, halo($C_1$-$C_4$)alkyl, halo($C_2$-$C_4$)alkenyl, halo($C_2$-$C_4$)alkynyl, halo($C_5$-$C_6$)cycloalkyl, ($C_1$-$C_2$)alkoxy($C_1$-$C_4$)alkyl, ($C_1$-$C_2$)alkoxy($C_2$-$C_4$)alkenyl, ($C_1$-$C_2$)alkoxy($C_2$-$C_4$)alkynyl, ($C_1$-$C_2$)alkoxy($C_5$-$C_6$)cycloalkyl, halo($C_1$-$C_2$)alkoxy($C_1$-$C_4$)alkyl, halo($C_1$-$C_2$)alkoxy($C_2$-$C_4$)alkenyl, halo($C_1$-$C_2$)alkoxy($C_2$-$C_4$)alkynyl, and halo($C_1$-$C_2$)alkoxy($C_5$-$C_6$)cycloalkyl, or $R^1$ and $R^2$ may together represent a ($C_4$-$C_5$)alkylene group or a ($C_4$-$C_5$)alkylene group substituted with one or two substituents each independently selected from the group consisting of ($C_1$-$C_2$)alkyl, ($C_1$-$C_2$)alkoxy, halo and halo($C_1$-$C_2$)alkoxy, so as to form a nitrogen-containing five or six membered cyclic ring with the nitrogen to which they attach, $R^3$ is ($C_1$-$C_8$)alkyl, halo($C_1$-$C_4$)alkyl or ($C_5$-$C_6$)cycloalkyl, phenyl, phenyl($C_1$-$C_6$)alkyl, or phenyl or phenyl($C_1$-$C_6$)alkyl both substituted on the phenyl ring with one to two substituents each independently selected from the group consisting of ($C_1$-$C_4$)alkyl, ($C_2$-$C_4$)alkenyl, ($C_2$-$C_4$)alkynyl, halo, halo($C_1$-$C_2$)alkyl, ($C_1$-$C_4$)alkoxy, halo($C_1$-$C_2$)alkoxy, cyano, nitro, ($C_1$-$C_4$)alkoxycarbonyl, ($C_1$-$C_2$)alkylthio and halo($C_1$-$C_2$)alkylthio, X is O or S and
Y is O.

4. The compound of claim 3 wherein $R^1$ and $R^2$ are each independently selected from the group consisting of ($C_1$-$C_3$)alkyl, ($C_2$-$C_4$)alkenyl and ($C_2$-$C_4$)alkynyl, or $R^1$ and $R^2$ may together represent a ($C_4$-$C_5$)alkylene group or a ($C_4$-$C_5$)alkylene group substituted with one or two substituents independently selected from methyl and ethyl, so as to form a nitrogen-containing five or six membered cyclic ring with the nitrogen to which they attach and $R^3$ is ($C_1$-$C_8$)alkyl, halo($C_1$-$C_4$)alkyl, phenyl or phenyl substituted with one to two substituents each independently selected from the group consisting of ($C_1$-$C_3$)alkyl, halo, halo($C_1$-$C_2$)alkyl, ($C_1$-$C_2$)alkoxy, halo($C_1$-$C_2$)alkoxy, cyano, nitro, ($C_1$-$C_2$)alkoxycarbonyl, ($C_1$-$C_2$)alkylthio and halo($C_1$-$C_2$)alkylthio.

5. The compound of claim 4 wherein $R^1$ and $R^2$ are each independently selected from the group consisting of methyl, ethyl, n-propyl, isopropyl, allyl and methallyl, or $R^1$ and $R^2$ may together with the nitrogen to which they attach represent a piperidyl group or a piperidyl group substituted with one or two methyl groups and $R^3$ is ethyl, neopentyl, 2,2-dichloroethyl, 2,2,2-trichloroethyl, 2,2,3,3,3-pentafluoropropyl, 2,2,2-trifluoroethyl, 1,3-difluoro-2-propyl, phenyl or phenyl substituted with one to two substituents each independently selected from the group consisting of chloro, fluoro, bromo, methyl, isopropyl, trifluoromethyl, methoxy, methylthio, nitro, cyano and methoxycarbonyl.

6. The compound of claim 5 wherein $R^1$ and $R^2$ are both ethyl, $R^3$ is phenyl, 3-methylphenyl, 4-methylphenyl, 4-(trifluoromethyl)phenyl, 4-fluorophenyl, 4-chlorophenyl, 3-methoxyphenyl, 4-methoxyphenyl, 4-(methylthio)phenyl, 2,2,2-trifluoroethyl or 1,3-difluoro-2-propyl and X is O.

7. The compound of claim 6 which is phenyl 1-(N,N-diethylcarbamoyl)-1,2,4-triazole-3-sulfonate;

3-methylphenyl 1-(N,N-diethylcarbamoyl)-1,2,4-triazole-3-sulfonate;

4-methylphenyl 1-(N,N-diethylcarbamoyl)-1,2,4-triazole-3-sulfonate;

4-(trifluoromethyl)phenyl 1-(N,N-diethylcarbamoyl)-1,2,4-triazole-3-sulfonate;

2,2,2-trifluoroethyl 1-(N,N-diethylcarbamoyl)-1,2,4-triazole-3-sulfonate;

4-fluorophenyl 1-(N,N-diethylcarbamoyl)-1,2,4-triazole-3-sulfonate;

4-methoxyphenyl 1-(N,N-diethylcarbamoyl)-1,2,4-triazole-3-sulfonate;

4-(methylthio)phenyl 1-(N,N-diethylcarbamoyl)-1,2,4-triazole-3-sulfonate; or 1,3-difluoro-2-propyl 1-(N,N-diethylcarbamoyl)-1,2,4-triazole-3-sulfonate.

8. A herbicidal composition which comprises an agronomically acceptable carrier and a herbicidally effective amount of the compound of claim 1.

9. A herbicidal composition which comprises an agronomically acceptable carrier and a herbicidally effective amount of the compound of claim 3.

10. A herbicidal composition which comprises an agronomically acceptable carrier and a herbicidally effective amount of the compound of claim 5.

11. A herbicidal composition which comprises an agronomically acceptable carrier and a herbicidally effective amount of the compound of claim 7.

12. A method for controlling unwanted plants which comprises applying to the plant or growth medium of the plants a herbicidally effective amount of the compound of claim 1.

13. A method for controlling unwanted plants which comprises applying to the plant or growth medium of the plants a herbicidally effective amount of the compound of claim 3.

14. A method for controlling unwanted plants which comprises applying to the plant or growth medium of the plants a herbicidally effective amount of the compound of claim 5.

15. A method for controlling unwanted plants which comprises applying to the plant or growth medium of the plants a herbicidally effective amount of the compound of claim 7.

* * * * *

UNITED STATES PATENT AND TRADEMARK OFFICE
CERTIFICATE OF CORRECTION

PATENT NO. : 5,211,739
DATED : May 18, 1993
INVENTOR(S) : Raul C.G. Lopez

It is certified that error appears in the above-indentified patent and that said Letters Patent is hereby corrected as shown below:

On the Title page, and in Col. 1, delete "-" between Herbicidal and 1-thisulfonates should be thiosulfonates Column 10, line 16, Tabel 1B, Ex. No. 13, under R3:
should be --$CH_2CCl_3$-- not "$C_2CCl_3$".

Signed and Sealed this

Twenty-fifth Day of January, 1994

*Attest:*

BRUCE LEHMAN

*Attesting Officer*     *Commissioner of Patents and Trademarks*